United States Patent [19]

Berté et al.

[11] Patent Number: 4,912,243

[45] Date of Patent: Mar. 27, 1990

[54] PROCESS OF PRODUCING A SILANIC OR SILOXANIC COMPOUND CONTAINING AT LEAST ONE CYCLOALKYL RING

[75] Inventors: Riccardo Berté, Vercelli; Francesco Gementi, Milan; Loris Sogli; Raffaele Ungarelli, both of Novara, all of Italy

[73] Assignee: Istituto Guido Donegani S.p.A., Novara, Italy

[21] Appl. No.: 186,349

[22] Filed: Apr. 26, 1988

[30] Foreign Application Priority Data

Apr. 30, 1987 [IT] Italy .............................. 20316 A/87

[51] Int. Cl.$^4$ .............................................. C07F 7/18
[52] U.S. Cl. ................................................... 556/466
[58] Field of Search ....................... 556/466; 585/269

[56] References Cited

U.S. PATENT DOCUMENTS 3,751,500 8/1973 Hall ..................................... 585/269

Primary Examiner—John Doll
Assistant Examiner—Stuart L. Hendrickson
Attorney, Agent, or Firm—Stevens, Davis, Miller & Mosher

[57] ABSTRACT

A process of producing a silanic or siloxanic compound containing at least one cycloalkyl ring by hydrogenation of a corresponding compound containing at least one aromatic ring, in solution, in the presence of a catalyst comprising palladium, supported on active carbon and at a pressure equal to or higher than 10 bar.

17 Claims, No Drawings

PROCESS OF PRODUCING A SILANIC OR SILOXANIC COMPOUND CONTAINING AT LEAST ONE CYCLOALKYL RING

DESCRIPTION OF THE INVENTION

The invention relates to a process for producing a silanic or siloxanic compound containing at least one cycloalkyl ring by catalytic hydrogenation of a corresponding compound containing at least one aromatic or heteroaromatic ring having the formula (I):

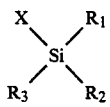

wherein:

X is an aryl, alkylaryl or arylalkyl group, having from 6 to 20 carbon atoms, and optionally containing, in the chain or in the ring, at least one hetero-atom selected from oxygen, sulphur and nitrogen and optionally, at least one halogen atom in place of a hydrogen atom, $R_1$, $R_2$ and $R_3$, which may be same or different, may have the same meaning as X or they may be hydrogen atoms, an alkyl or alkylene radical containing from 1 to 20 carbon atoms, a linear or branched alkyl radical having from 1 to 20 carbon atoms and containing one or more alkoxyl or carboxyl groups, or an $N(R')_2$ group, in which $R'$ is a hydrogen atom or an alkyl radical containing from 1 to 20 carbon atoms.

The catalytic hydrogenation of tolyl-triethoxy-silane having the formula (II):

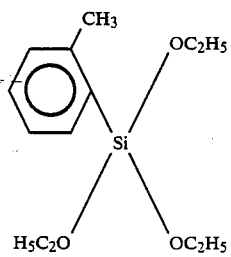

is known from the journal of the American Chemical Society, Volume 84, May 20, 1962, pages 1856–1868. Such hydrogenation is carried out in the presence of a Raney nickel catalyst at a temperature ranging from 95° to 105° C. over 16 hours, and at a pressure of 1,000 p.s.i., thereby obtaining a yield of about 50%.

This process is not industrially acceptable as far as the yield and productivity are concerned; moreover, it has the drawback of requiring high pressures for carrying out the hydrogenation. Moreover, one noted that the yield level decreased to even lower values in the case of hydrogenation of some aryl alkoxy-silanes that are highly useful from an industrial point of view, by using the same operating conditions described in the above-mentioned publication. Moreover, it was virtually impossible, till now, to avoid a massive hydrogenolysis of the carbon-silicon bonds.

It has now been discovered, in accordance with the present invention, that there is a particular kind of catalyst leading to excellent and quite unexpected yields, not only in the case of tolyl-triethoxy-silane of the formula (II), but also more generally in the case of silanic or siloxanic compounds of the formula (I), which, till now, could not be hydrogenated, or were hydrogenated only at the cost of negligible yields, with considerable losses owing to hydrogenolysis and under burdensome operating conditions.

Therefore this invention, in its widest aspect, relates to a process for producing a silanic or siloxanic compound containing at least one cycloalkyl ring by catalytic hydrogenation of a corresponding aryl-derivative of the formula (I), wherein the hydrogenation is carried out in solution, at a pressure of at least 10 bar, and in the presence of catalytic quantities of a catalyst consisting or consisting essentially of palladium supported on active carbon.

The active carbon used as a carrier for the palladium is per se a known product; it generally has a specific surface lower than 1,000 $m^2/g$, and more particularly between 400 and 900 $m^2/g$, and preferably between 600 and 800 $m^2/g$.

The catalyst may be prepared according to anyone of the general methods which may be found in the literature such as, for example, the method described in H. Gilman "Organic Chemistry", Vol. 1, pages 780–789, 2nd Edition, J. Wiley & Sons, New York, 1953.

The quantity of palladium in the catalyst is not critical and is preferably between 0.2 and 20% by weight calculated on the dry catalyst. However, quantities higher than 20% by weight may also be used.

These catalysts comprising palladium supported on active carbon are well known on the market. They are produced and sold by the Dutral Company of Milano (ITALY) under the trade marks MPT/1, MPT/2, MPT/3 etc. up to MPT/10.

According to the process of the present invention, the hydrogenation is carried out in the presence of an organic solvent, preferably an apolar solvent, such as for instance a saturated hydrocarbon, such as n-hexane or cyclohexane.

The amount of solvent ranges generally from 0.1 to 10 kg per kg of the substrate of the formula (I) that is to be hydrogenated.

The amount of catalyst to be used in the process of the present invention is not critical, and may range from 0.2 to 2% by weight of palladium with respect to the product of the formula (I) that is to be hydrogenated.

The hydrogenation is carried out at a temperature of at least 90° C., and preferably from 100° to 150° C., at a pressure of at least 10 bar, and preferably from 16 to 120 bar, and with a reaction time ranging from 0.5 to 50 hours, and preferably from 1 to 20 hours.

The commercial importance of the invention will be even more appreciated considering that the cycloalkyl derivatives of silanes and siloxanes were obtained industrially, till now, through a complicated process that used cyclohexene as the raw starting material. See on this subject the article in the Journal of Organometallic Chemistry, Vol. 121 (1976), page 40.

A non-limitative list of silanes and siloxanes which may be obtained by the process of the present invention is as follows:

(cyclohexyl)—Si—$(OCH_3)_3$;
(cyclohexyl)$_2$—Si—$(OCH_3)_2$;

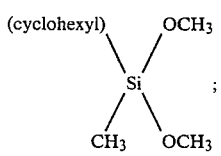

(cyclohexyl)—Si—(OC$_2$H$_5$)$_3$;
(cyclohexyl)$_2$—Si—(OC$_2$H$_5$)$_2$;

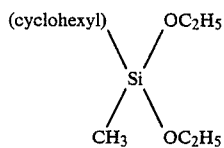

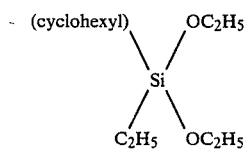

1,3-dicyclohexyl-tetramethyl-disiloxane;
tetracyclohexyl-oxysilane;
tetracyclohexyl-silane;
cyclohexyl-methylen-trimethyl-silane The silanes and siloxanes obtained according to the present invention may be used advantageously for preparing catalysts for olefin polymerization. They are used directly as a component of the olefin polymerization catalyst, by reacting the end products of the process of the present invention with the other catalyst component, e.g., see EP Nos. 45,975; 45,976 and 45,977.

The following examples will illustrate the invention but without limiting its scope.

EXAMPLES 1–4

An amount, as set forth in Table 1, of a catalyst constituted by palladium supported on active carbon, sold by DUTRAL Company under the trade name MPT/5, containing 5% by weight of palladium, was loaded, in the form of a suspension in n-hexane at 30% by weight, into an autoclave having a volume of 500 cm$^3$. Then methyl-phenyl-dimethoxy-silane and the solvent were added in the amount, as set forth in the Table, till the volume reached 200 cm$^3$. The mixture was then heated gradually over one hour, under strong stirring, at the temperature and the hydrogen pressure, as set forth in Table 1. After the reaction times indicated hereinbefore, the hydrogenation was practically over. The final mass was cooled, the catalyst was separated by decantation and filtration then the solvent was evaporated. Di-cyclohexyl-dimethoxy-silane was obtained, having a purity of 99.6% and in the amount and with yields as set forth in Table 1.

TABLE 1

| Examples | 1 | 2 | 3 | 4 |
|---|---|---|---|---|
| Catalyst (g) | 36 | 30 | 22.6 | 44.9 |
| Di-phenyl-dimethoxy-silane (DMPS); (g) | 150 | 150 | 150 | 150 |
| Solvent | n-hexane | n-hexane | n-hexane | n-hexane |
| T (°C.) | 90–125 | 90–105 | 90–100 | 94–130 |
| H$_2$ Pressure (bar) | 16–100 | 36–40 | 16–60 | 16–50 |
| Catalyst/DMPS Ratio (g/kg) | 240 | 200 | 151 | 299 |
| Solvent/DMPS Ratio (kg/kg) | 0.8 | 0.8 | 0.8 | 0.8 |
| Time | 2 h 20' | 4 h | 7 h | 2 h 30' |
| Di-cyclohexyl-dimethoxy-silane (g) | 125.9 | 154 | 148.7 | 146.8 |
| Yield | 96.8 | 97.5 | 94.1 | 92.9 |

EXAMPLES 5–11

By operating according to the procedure of the preceding examples and by using the same MPT/5 catalyst, the hydrogenation of other silane or siloxane derivatives of the formula (I) was carried out. In Table 2 there are reported the compounds subjected to hydrogenation, the catalyst amounts, the solvent type, the pressure, the temperature, the reaction time, as well as the products obtained and the relevant amounts and yields:

TABLE II

| EXAMPLES | 5 | 6 | 7 | 8 | 9 | 10 | 11 |
|---|---|---|---|---|---|---|---|
| Catalyst (g) | 24 | 30 | 32 | 20 | 35 | 25 | 36 |
| Phenyl methyldimethoxy silane (g) | 150 | 150 | 133 | — | — | — | — |
| Phenyl trimethoxy silane (g) | — | — | — | 80 | — | — | — |
| Phenyl triethoxy silane (g) | — | — | — | — | 139.5 | — | — |
| Benzyl trimethyl silane (g) | — | — | — | — | — | 135 | — |
| 1,3 diphenyl tetramethyl disiloxane | — | — | — | — | — | — | 240 |
| Solvent | n hexane | cyclo hexane | ethyl acetate | n hexane | n hexane | n hexane | n hexane |
| T (°C.) | 90–100 | 95–110 | 105 | 100–110 | 95–110 | 100–115 | 110–120 |
| H$_2$ Pressure (bar) | 16–60 | 20–60 | 16 | 20–50 | 16–70 | 30–50 | 16–70 |
| Catalyst/silane ratio | 160 | 200 | 241 | 250 | 251 | 185 | 150 |
| Solvent/silane ratio | 0.8 | 0.7 | 1.2 | 2.4 | 0.8 | 1.6 | 0.2 |
| Time (h) | 3 | 2 | 4 | 2 | 3 | 3 | 4 |
| Cyclohexyl methyl dimethoxy silane (g) | 152.4 | 149.3 | 125.5 | — | — | — | — |
| Cyclohexyl trimethoxy silane (g) | — | — | — | 81.1 | — | — | — |
| Cyclohexyl triethoxy silane (g) | — | — | — | — | 139.3 | — | — |
| Cyclohexyl methylentrimethyl silane | — | — | — | — | — | 133.4 | — |
| 1,3' dicyclohexyltetramethyldisiloxane | — | — | — | — | — | — | 231.9 |
| Yield (%) | 98 | 96 | 91 | 98 | 97 | 95 | 92 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

What is claimed is:

1. A process for producing a silanic or siloxanic compound containing at least one cycloalkyl ring by catalytic hydrogenation of a corresponding silanic or siloxanic compound containing at least one aromatic compound ring having the formula (I):

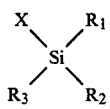 (I)

wherein:
X is a hydrocarbon aryl, alkylaryl or arylalkyl group having from 6 to 20 carbon atoms;
$R_1$, $R_2$ and $R_3$, may be the same or different and are selected from the group consisting of those groups of the same meaning as X, hydrogen atoms, an alkyl or alkylene radical contain from 1 to 20 carbon atoms, a linear or branched alkyl radical having from 1 to 20 carbon atoms and containing one or more alkoxyl, carbonyl or carboxyl group and an $N(R')_2$ group, in which R' is a hydrogen atom or an alkyl radical containing from 1 to 20 carbon atoms, characterized in that the hydrogenation is carried out in the presence of an organic solvent, at a pressure greater than 10 bar up to 120 bar and in the presence of a catalytic amount of a catalyst comprising palladium supported on active carbon.

2. A process according to claim 1, wherein the active carbon has a specific surface area lower than 1,000 m²/g.

3. A process according to claim 2, wherein the active carbon has a specific surface area between 400 and 900 m²/g.

4. A process according to claim 1, 2 or 3, wherein the palladium content in the catalyst is between 0.2 and 2% by weight, determined on the dry catalyst.

5. A process according to claim 1, 2 or 3, wherein the amount of the catalyst is between 0.2 and 2% by weight of palladium determined with reference to the product of the formula (I) that has to be hydrogenated.

6. A process according to claim 1, 2 or 3, wherein the hydrogenation is carried out in the presence of an organic solvent.

7. A process according to claim 6, wherein the organic solvent is apolar.

8. A process according to claim 7, where the apolar organic solvent is n-hexane or cyclohexane.

9. A process according to claim 1, 2 or 3, wherein the amount of the solvent is between 0.1 and 10 kg per kg of the product of the formula (I) that has to be hydrogenated.

10. A process according to claim 1, 2 or 3, wherein the hydrogenation is carried out at a temperature of at least 90° C., up to 150° C.

11. A process according to claim 2 or 3, wherein the hydrogenation is carried at a hdyrogen pressure of at least 10 bar, up to 120 bar.

12. A process according to claim 1, 2 or 3, wherein the reaction time ranges from 0.5 to 50 hours.

13. A process according to claim 1, wherein X contains at least one halogen atom in place of a hydrogen atom.

14. A process according to claim 3, wherein the active carbon has a specific surface area between 600 and 800 m²/g.

15. A process according to claim 10, wherein the temperature ranges from 100° C. to 150° C.

16. A process according to claim 11, wherein the hydrogen pressure is from 16 to 120 bar.

17. A process according to claim 12, wherein reaction time ranges from 1 to 20 hours.

* * * * *